US008656756B2

(12) United States Patent
Mizutani et al.

(10) Patent No.: US 8,656,756 B2
(45) Date of Patent: Feb. 25, 2014

(54) GAS SENSOR

(75) Inventors: Masaki Mizutani, Aichi (JP); Shigeki Mori, Seki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 331 days.

(21) Appl. No.: 12/253,265

(22) Filed: Oct. 17, 2008

(65) Prior Publication Data

US 2009/0100907 A1   Apr. 23, 2009

(30) Foreign Application Priority Data

Oct. 17, 2007   (JP) ................................ 2007-270607
Aug. 19, 2008   (JP) ................................ 2008-210347

(51) Int. Cl.
*G01N 7/00*   (2006.01)

(52) U.S. Cl.
USPC ......... 73/31.05; 73/23.2; 73/30.01; 73/30.02; 73/30.07

(58) Field of Classification Search
USPC ................... 73/23.5, 30.01–31.07
See application file for complete search history.

(56) References Cited

U.S. PATENT DOCUMENTS

| 7,415,877 | B2 * | 8/2008 | Okumura et al. | 73/431 |
| 7,607,340 | B2 * | 10/2009 | Nakashima et al. | 73/31.05 |
| 2006/0288759 | A1 * | 12/2006 | Okumura et al. | 73/31.05 |
| 2007/0084724 | A1 | 4/2007 | Mori et al. | |
| 2007/0245803 | A1 * | 10/2007 | Tan et al. | 73/31.05 |

FOREIGN PATENT DOCUMENTS

| JP | 9-105735 A | 4/1997 |
| JP | 9-203717 A | 8/1997 |
| JP | 10-170474 A | 6/1998 |
| JP | 2001-281208 A | 10/2001 |
| JP | 2002-365258 A | 12/2002 |
| JP | 2006-058144 A | 3/2006 |
| JP | 2006-250537 A | 9/2006 |
| JP | 2007-033374 A | 2/2007 |
| JP | 2007-139749 A | 6/2007 |

OTHER PUBLICATIONS

Office Action, dated Apr. 16, 2013, issued by the Japanese Patent Office in counterpart Japanese Patent Application No. 2008-210347.

* cited by examiner

*Primary Examiner* — Hezron E Williams
*Assistant Examiner* — Rodney T Frank
(74) *Attorney, Agent, or Firm* — Sughrue Mion, PLLC (57) ABSTRACT

A gas sensor including a metal shell; a detection element main body held by the metal shell; a porous protection layer coated on a leading end portion of the detection element main body; and a protector including a side wall surrounding an element protruding portion of the detection element main body protruding from a leading end of the metal shell. The side wall has introduction holes formed therein which allow gas to be introduced. The porous protection layer includes a first portion; and a second portion provided on a base end side with respect to the first portion and having a progressively reduced thickness in a direction toward a leading end of the detection element. The second portion is disposed closer to the base end of the detection element than the introduction holes in the axial direction.

10 Claims, 8 Drawing Sheets

GAS SENSOR

BACKGROUND OF THE INVENTION

1. Field of the Invention

The present invention relates to a gas sensor including a cylindrical metal shell extending in an axial direction and a detection element main body extending in the axial direction and attached at the diametrical inner side of the metal shell, and in particular, to a gas sensor including a porous protection layer that covers a leading end side in the axial direction of the detection element main body.

2. Description of the Related Art

The use of a gas sensor attached to an exhaust pipe of an automobile and including a detection element configured to vary an electromotive force or a resistance value according to the concentration of a specified component (for example, nitrogen oxide, oxygen, etc.) of exhaust gas is known.

The leading end portion of the detection element main body is coated with a porous protection layer including porous ceramic so as to prevent cracking that can occur due to thermal shock generated when water drops in exhaust gas adhere to the detection element. The porous protection layer disperses and slowly absorbs the water drops adhering to the detection element. Therefore, a large thermal shock is hardly generated at the detection element main body, and it is thus possible to prevent cracking of the detection element main body. For example, JP-A-2007-33374 (FIG. 1 and related description of this reference) discloses a gas sensor having such a protection layer.

However, the base end of the porous protection layer has a sharp corner part which may chip when subjected to vibration and shock in use. When water drops in exhaust gas adhere to a thinned or exposed portion of the porous protection layer due to such a chip, a crack may occur at the thinned or exposed portion of the detection element main body.

SUMMARY OF THE INVENTION

The present invention was made in consideration of the above circumstances, and an object thereof is to provide a gas sensor having a detection element main body which resists cracking due to the occurrence of chips at the base end of the porous protection layer.

According to a first aspect, the present invention provides a gas sensor which includes: a cylindrical metal shell extending along an axial direction from a leading end thereof to a base end thereof; a plate-shaped detection element main body extending along the axial direction from a leading end thereof to a base end thereof and held radially inside the metal shell, the detection element main body comprising an element protruding portion protruding from the leading end of the metal shell in the axial direction; a porous protection layer coated on a leading end portion of the detection element main body; and a protector attached to the metal shell and comprising a side wall surrounding the element protruding portion in a radial direction perpendicular to the axial direction, the side wall having introduction holes formed therein which allow gas to be introduced into an inner space defined by the sidewall, wherein the porous protection layer comprises: a first portion; and a second portion provided on a base end side with respect to the first portion, the second portion having a progressively reduced or rather gradually reducing thickness in a direction toward the base end of the detection element, and wherein the second portion of the porous protection layer is disposed closer to the base end of the detection element than the introduction holes in the axial direction.

In the gas sensor according to this aspect of the invention, the second portion of the porous protection layer, which is positioned on a base end side relative to the first portion, is shaped such that the thickness thereof gradually thins toward the base end side. That is, the second portion has no sharp corner parts differing from the base end of the related-art porous protection layer. Therefore, it is possible to prevent chipping at the second portion when the gas sensor is subjected to vibration and shock in use; to prevent the porous protection layer at the chipped portion from thinning; and to prevent the detection element main body from being exposed at the chipped portion. Accordingly, the detection element main body is not susceptible to cracking even if water drops in exhaust gas adhere to the second portion.

Furthermore, because the second portion is disposed on the base end side relative to the introduction holes formed at the sidewall of the protector surrounding the element protruding portion, water drops hardly pass through the introduction holes to adhere to the second portion. Therefore, the gas sensor can reliably prevent cracking of the detection element main body.

The second portion of the porous protection layer is shaped such that the thickness thereof is gradually reduced toward the base end side. Examples of the shape of the second portion, in which the thickness is gradually reduced toward the base end side, include a tapered shape, an R shape (rounded shape), etc.

The first portion of the porous protection layer coats the periphery of the detection element main body from the leading end of the detection element main body to the second portion. The protector may be any of a single-structure protector and a multiple-structure protector in which two or more protectors are stacked. In the multiple-structure protector, the protector located at the innermost side and directly (i.e., where no other protector is present between the protector and the detection element) surrounding the detection element main body corresponds to the "protector" defined in this aspect of the invention.

In a second aspect of the invention, the gas sensor of the first aspect may be shaped so that the length in the axial direction of the second portion of the porous protection layer is not less than the thickness of the first portion of the porous detection layer but not more than 3 mm.

Since the length in the axial direction of the second portion of the porous protection layer is not less than the thickness of the first portion but not more than and including 3 mm, it is possible to reliably prevent cracking at the second portion when the gas sensor is subjected to vibration and shock in use. Therefore, a gas sensor of high reliability can be provided so as to effectively prevent cracking of the detection element main body.

In a third aspect, the invention provides a gas sensor of the first or second aspects, wherein the thickness of the first portion is not less than 100 μm but not more than 600 μm.

If the thickness of the first portion of the porous protection layer is too thin, e.g., less than 100 μm, there is a concern that sufficient effects required of the porous protection layer, for example, preventing the detection element main body from cracking when subjected to thermal shock when water drops adhere to the porous protection layer, cannot be obtained. On the other hand, if the first portion of the porous protection layer is too thick, e.g., more than 600 μm, since heat during a temperature rise of the heater is transferred to the porous protection layer, thermal activation of the detection element main body may be delayed. Consequently, the consumption power of the gas sensor heater increases, and the detection sensitivity of the gas sensor is reduced.

In contrast, since the thickness of the first portion of the porous protection layer is not less than 100 μm in the gas sensor according to the third aspect, sufficient effects can be obtained in that the porous protection layer can prevent the occurrence of cracks in conjunction with the adhesion of water drops. Also, because the thickness of the first portion of the porous protection layer is not more than 600 μm, the time that it takes to activate the detection element can be sufficiently shortened, and the consumption power of the heater can be reduced. In addition, the detection sensitivity of the gas sensor is enhanced.

In a fourth aspect, the invention provides a gas sensor of any of the first to third aspects, wherein the first portion has a smoothly curved outer shape in cross section. In other words, the first portion smoothly covers the element protruding portion.

In the gas sensor of the fourth aspect, the first portion of the porous protection layer smoothly covers the element protruding portion of the detection element main body. That is, because the detection element main body is plate-shaped, the element protruding portion having a top part formed by three surfaces has ridges (sides) formed by the main surface (plate surface) and a side surface, the main surface and the leading end surface. Even though the element protruding portion has this structure, the first portion of the porous protection layer, which coats the element protruding portion, has an entire outer surface shaped so as to be smooth and free from any sharp corner parts. Therefore, it is possible to effectively prevent cracking of the first portion when the gas sensor is subjected to vibration and shock in use. Accordingly, a gas sensor of higher reliability can be obtained.

In a fifth aspect, the invention provides a gas sensor of any of the first to fourth aspects, wherein the minimum clearance between the first portion and the protector is 0.5 mm or more.

If the minimum clearance between the first portion and the protector is too small, e.g., less than 0.5 mm, water drops entering the interior of the protector along with the gas to be measured are apt to adhere so as to accumulate between the protector and the first portion. Also, water drops once adhered onto the inner circumferential surface of the protector may move on the inner circumferential surface and adhere to the first portion.

In contrast, in the fifth aspect, even if water drops enter the interior of the protector along with the gas to be measured, since the minimum clearance between the detection element and the protector is 0.5 mm or more, water drops hardly adhere to the first portion. Further, even if water drops once adhered to the inner circumferential side of the protector move, the water drops hardly adhere to the first portion. Therefore, it is possible to reliably prevent cracking of the detection element main body due to thermal shock when water drops adhere.

According to a sixth aspect, the invention provides a gas sensor of any of the first to fifth aspects, wherein the second portion is disposed in the metal shell.

In the gas sensor according to the sixth aspect, the second portion is disposed inside the metal shell. Therefore, water drops hardly adhere to the second portion since the metal shell serves as a barrier. Therefore, the sixth aspect provides a gas sensor in which cracking of the detection element main body can be effectively prevented.

According to a seventh aspect, the invention provides a gas sensor of the sixth aspect, wherein the minimum clearance between the metal shell and the first portion is 1.45 mm or less.

If the minimum clearance between the metal shell and the first portion is too large, e.g., more than 1.45 mm, water drops that enter the interior of the protector along with the gas to be measured are apt to enter the clearance between the metal shell and the detection element main body (the second portion). As a result, water drops tend to adhere to the second portion.

In contrast, even if water drops enter the interior of the protector along with gas to be measured, since in the seventh aspect the minimum clearance between the metal shell and the first portion is 1.45 mm or less, the water drops hardly adhere to the second portion. Therefore, it is possible to reliably prevent cracking of the detection element main body due to thermal shock when water drops adhere.

In an eighth aspect, the invention provides a gas sensor of the sixth or seventh aspects, wherein the distance between the second portion and the leading end of the metal shell is greater than the minimum clearance between the metal shell and the first portion. Therefore, even if water drops enter the interior of the protector along with gas to be measured, the water drops hardly adhere to the second portion. Accordingly, it is possible to reliably prevent cracking of the detection element main body due to thermal shock when water drops adhere. According to ninth aspect, it is preferable that, in the gas sensor of any of the sixth to eighth aspects, the minimum clearance between the metal shell and the first portion is smaller than the diameter of the introduction holes.

DESCRIPTION OF THE EMBODIMENTS

Figure 1:
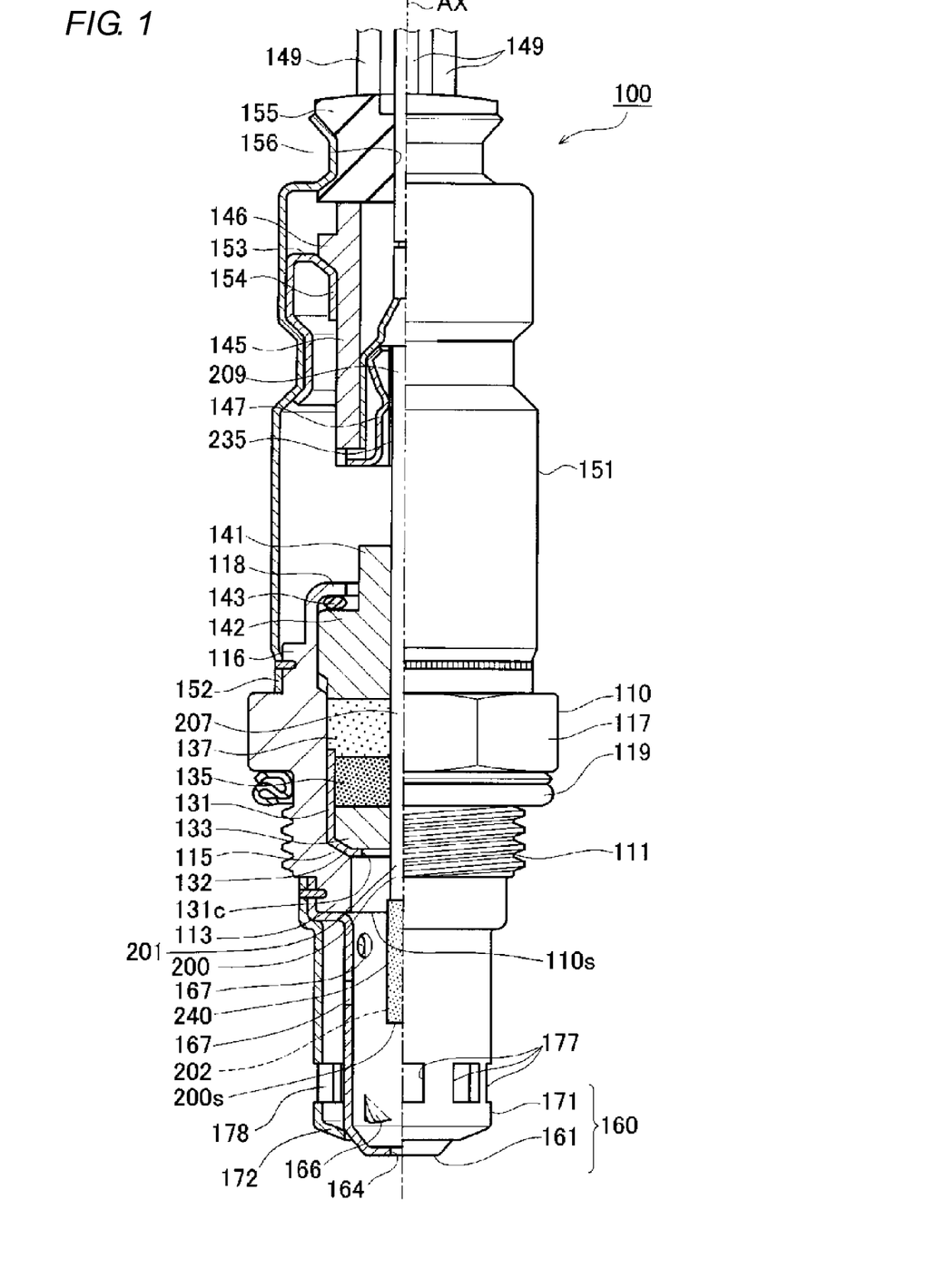
FIG. 1 is a partial sectional view showing a sensor according to an embodiment of the invention.
Figure 2:
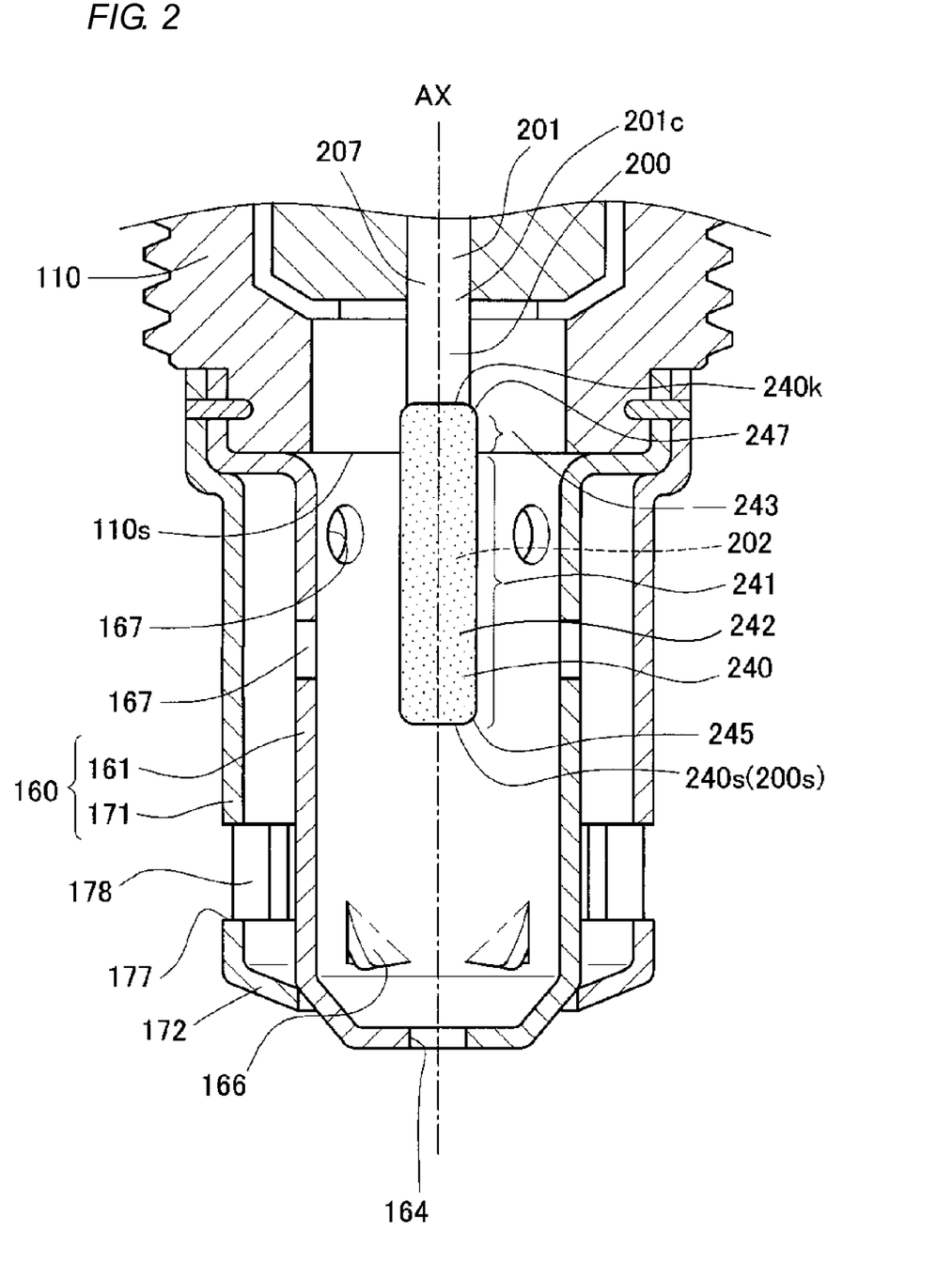
FIG. 2 is a sectional view, observed from the side surface side of a detection element, of the leading end side portion of the gas sensor according to the embodiment.
Figure 3:
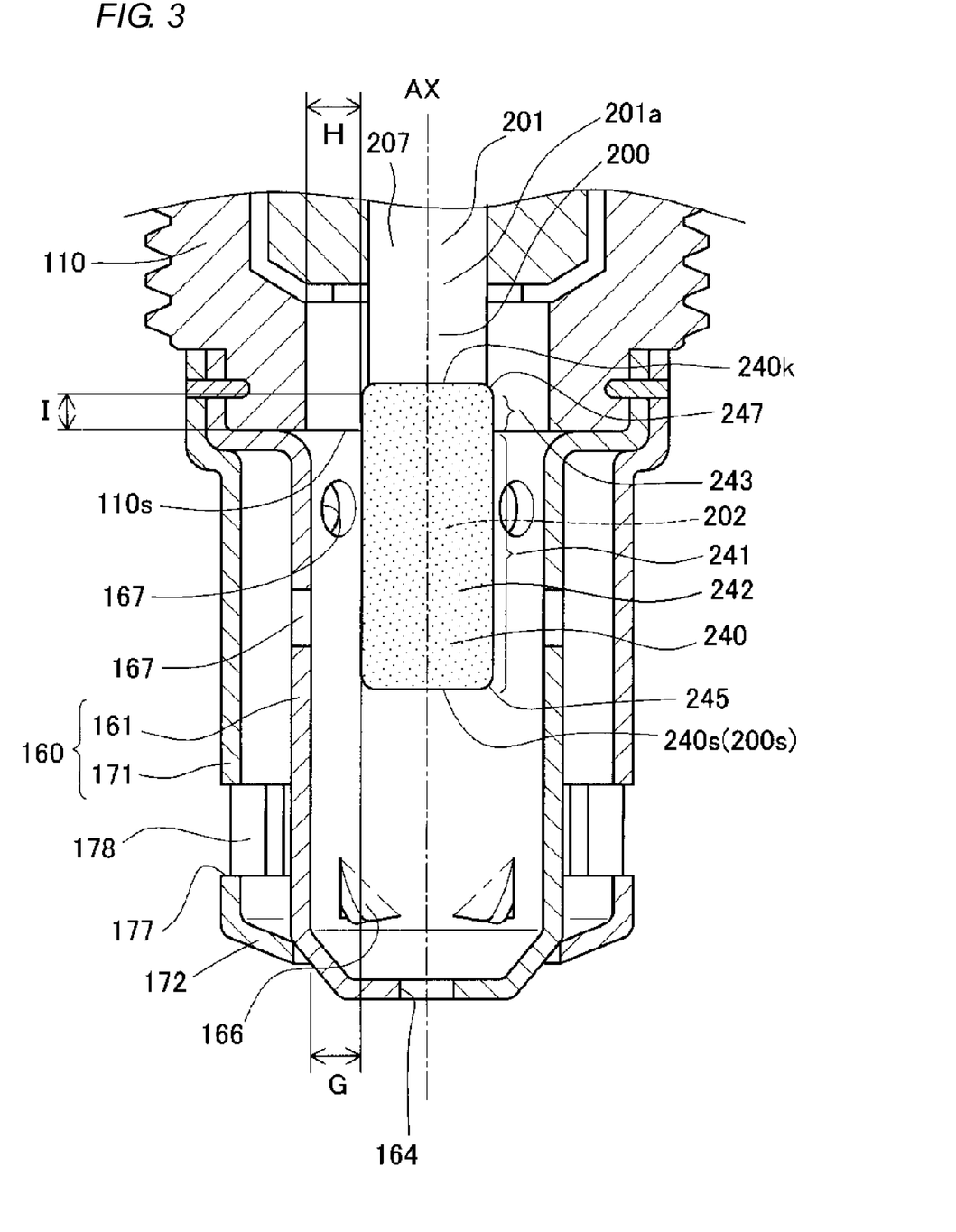
FIG. 3 is a sectional view, observed from the plate surface side of a detection element, of the leading end side portion of the gas sensor according to the embodiment.
Figure 4:
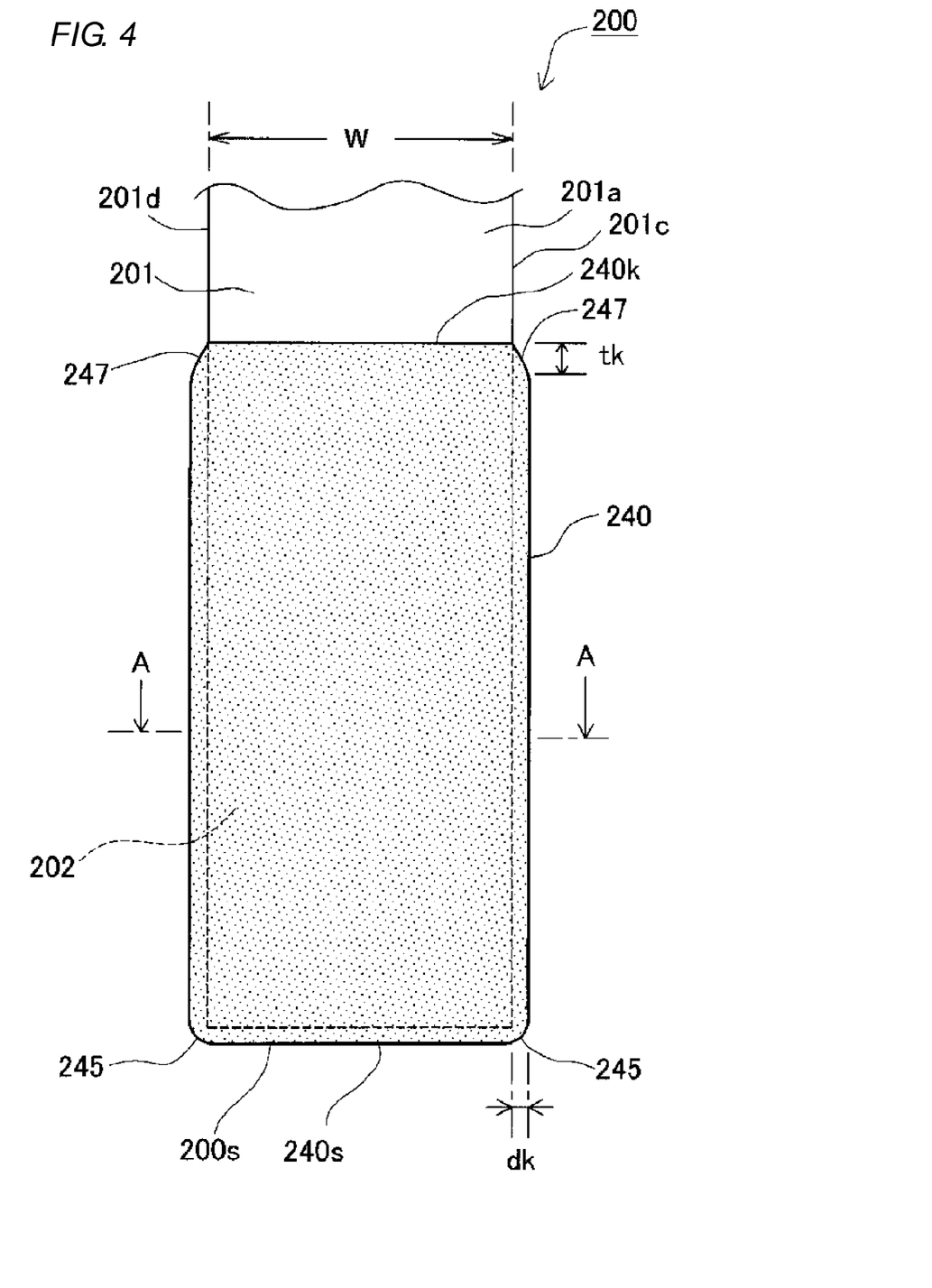
FIG. 4 is a plan view showing a leading end side portion of the detection element of the gas sensor according to the embodiment.
Figure 5:
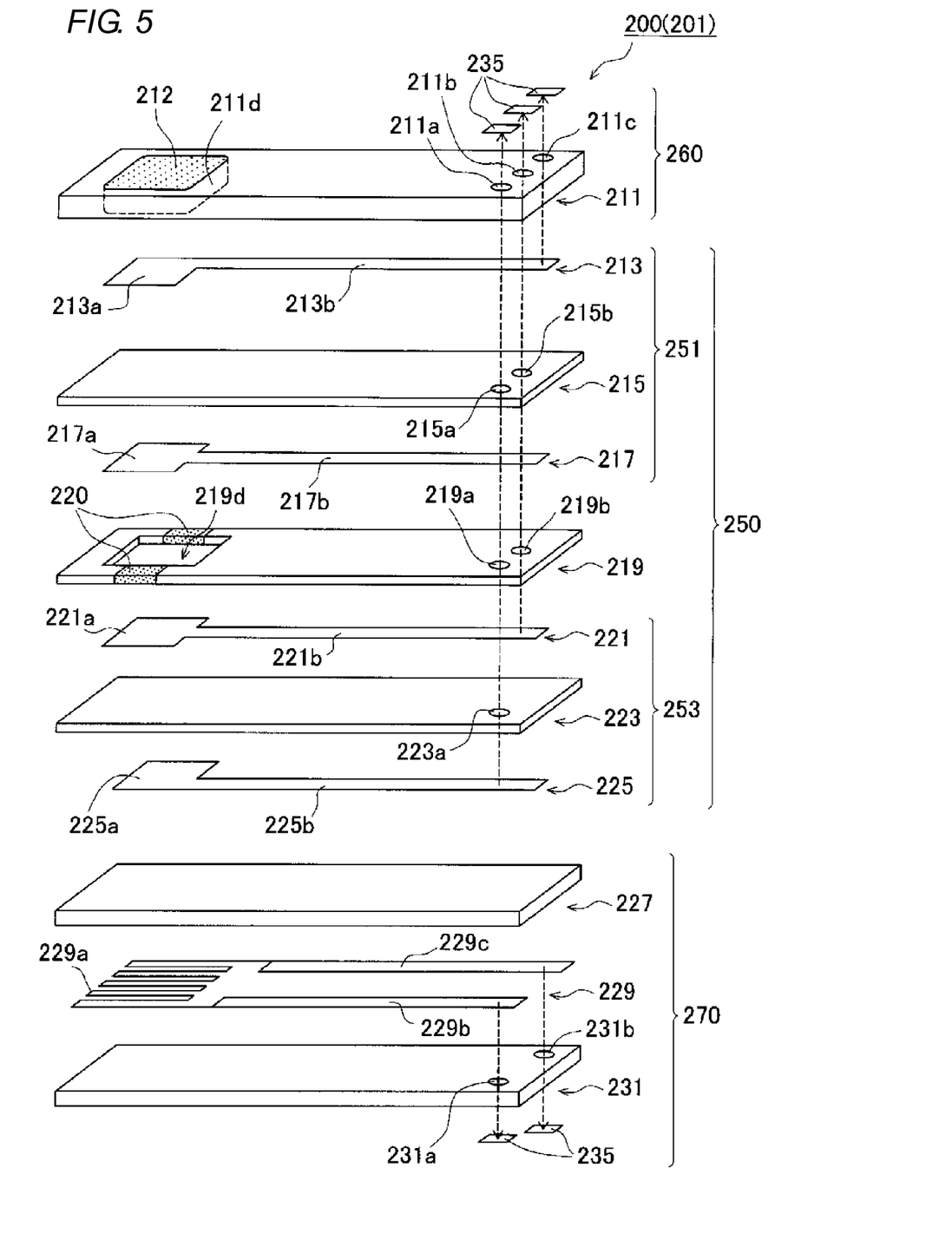
FIG. 5 is a disassembled perspective view showing a detection element main body of a detection element of the gas sensor according to the embodiment.
Figure 6:
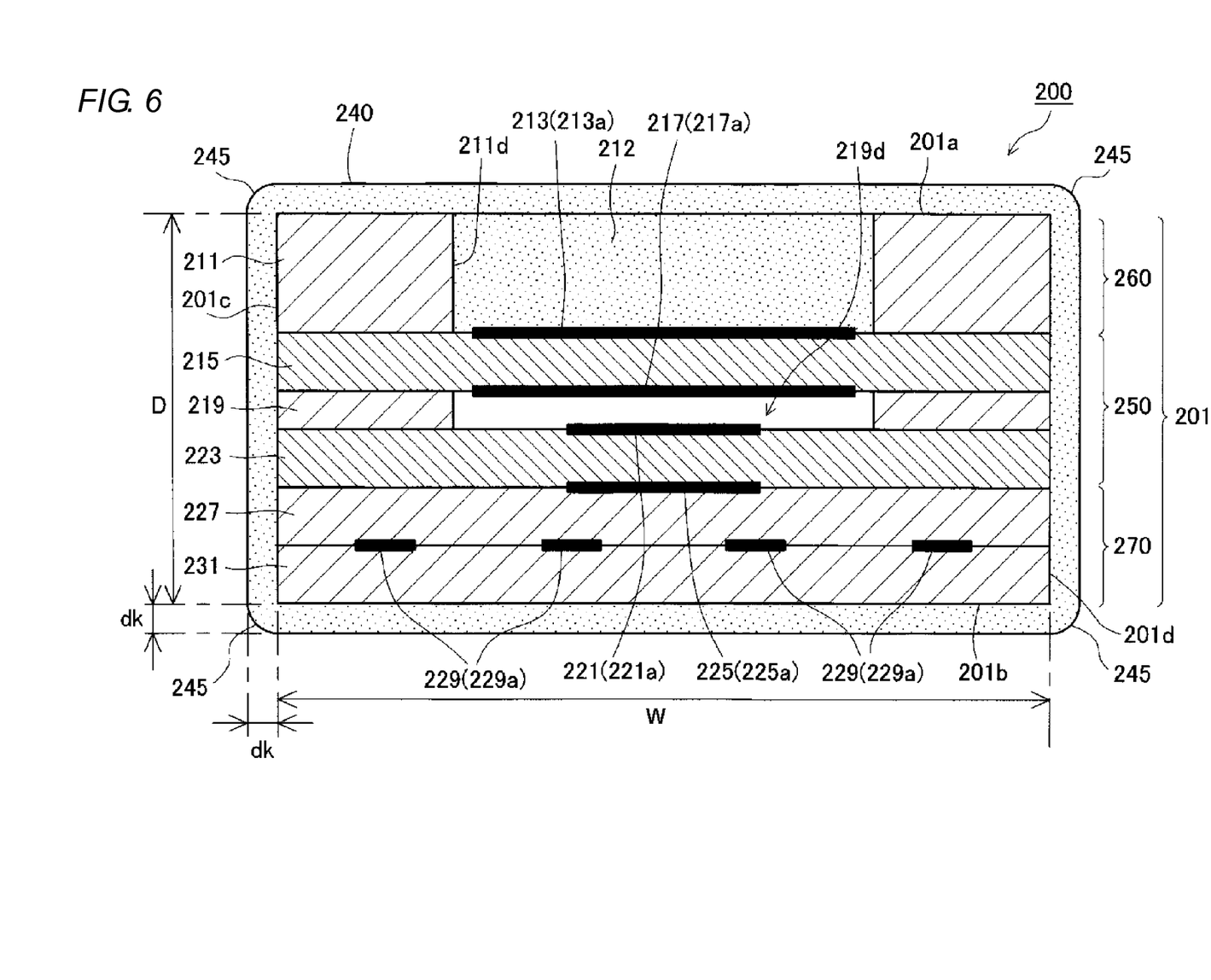
FIG. 6 is a cross-sectional view (sectional view taken along the line A-A in FIG. 4) of the leading end side portion of the detection element of the gas sensor according to the embodiment.

An embodiment of the present invention is described with reference to the drawings. However, the present invention should not be construed as being limited thereto. FIG. 1 shows a gas sensor 100 according to an embodiment of the invention. FIG. 2 and FIG. 3 are enlarged views showing the leading end side portion of the gas sensor 100. FIG. 4 is a plan view showing the leading end side portion of a detection element 200 of the gas sensor 100. FIG. 5 is a perspective view showing a detection element main body 201 of the detection element 200. FIG. 6 is a cross-sectional view (section taken along the line A-A in FIG. 4) showing the leading end side portion of the detection element 200. In FIG. 1 through FIG. 4, the underside of the drawing sheet corresponds to the leading end side with respect to the axis AX direction (hereinafter also called the "leading end side"), and the upper side thereof corresponds to the base end side with respect to the axis AX direction (hereinafter also called the "base end side"). In FIG. 5, the left side corresponds to the leading end side, and the right side corresponds to the base end side.

The embodiment shows, as an example of he gas sensor 100, a full-range air-fuel ratio sensor attachable to an exhaust pipe of an automobile (not illustrated) for measuring the air-fuel ratio of exhaust gas based on the concentration of oxygen (specified gas constituent) contained in the exhaust gas. In the embodiment, the detection element 200 is provided at the interior of the exhaust pipe and exposed to exhaust gas (the gas to be detected) flowing in the exhaust pipe. As shown in FIG. 1, the gas sensor 100 includes: a cylindrical metal shell 110 extending in a direction parallel to the axis AX (hereinafter referred to as the "axis AX direction" or "axial direction"); a plate-shaped detection element 200 attached to the interior of the metal shell 110; an outer cylinder 151 fixed at the base end side of the metal shell 110; and a protector 160 fixed at the leading end side of the metal shell 110.

The detection element 200 includes a detection element main body 201 having a plate (strip) shape extending along the axis AX direction and having a width (W) (e.g., 4 mm) and thickness (D) (e.g., 1.5 mm) (see FIG. 6). The detection element main body 201 has a first plate surface 201*a*, a second plate surface 201*b*, a first side surface 201*c* and a second side surface 201*d* (see FIG. 4 and FIG. 6). As shown in FIG. 1, the detection element main body 201 includes: an element protruding portion 202 protruding from a leading end side opening end 110*s* of the metal shell 110 toward the leading end side (downward in the drawing); a barrel portion 207, the circumference in the diametrical direction of which is enclosed by the metal shell 110; and an element base end portion 209 protruding from the metal shell 110 toward the base end side (upward in the drawing).

A cylindrical, bottomed and metal-containing cup 131 (hereinafter referred to as a metallic cup 131) is disposed at a position slightly deviated to the leading end side from the middle of the barrel portion 207 of the detection element 200, such that the detection element 200 is inserted into the opening 131*c* formed at the bottom of the metallic cup 131, and the leading end side portion of the detection element 200 protrudes from the opening 131*c*. The metallic cup 131 holds the detection element 200 in the metal shell 110 and has a leading end circumferential edge portion 132 which is tapered such that the diameter of the metallic cup 131 is reduced toward the leading end side. An alumina-containing ceramic ring 133 and a first talc ring 135 formed by a compressed talc powder are accommodated in the metallic cup 131 in a state where the detection element 200 is inserted into the metallic cup 131. The first talc ring 135 is crushed in the metallic cup 131 and is thoroughly filled therein. Therefore, the detection element 200 is positioned and held in the metallic cup 131.

The detection element 200 integrated with the metallic cup 131 is held such that the radial periphery of the detection element is surrounded by the cylindrical metal shell 110. The metal shell 110 attaches and fixes the gas sensor 100 to the exhaust pipe of an automobile and may be made of a low-carbon stainless steel such as SUS403. A male threaded portion 111 for attaching to the exhaust pipe is formed at the leading end side of the outer circumference of the metal shell 110. The metal shell 100 includes a protruding annular-shaped leading end fixing portion 113 at the leading end side from the male threaded portion 111 and the protector 160 is fixed thereto.

The metal shell 119 further includes a tool engaging portion 117 at the center of the outer circumference of the metal shell 110 for engaging an attaching tool. A gasket 119 for preventing loss of gas when attached to an exhaust pipe is inserted and fitted between the tool engaging portion 117 and the male threaded portion 111. Further, a base end fixing portion 116 formed at the base end side of the tool engaging portion 117 allows an outer cylinder 151 to be fixed thereon. A crimping portion 118 which crimps and holds the detection element 200 in the metal shell 110 is formed on the base end side relative to the base end fixing portion 116.

A stepped portion 115 having a tapered shape, the diameter of which is reduced toward the leading end side, is formed at the leading end side of the inner circumference of the metal shell 110. The leading end circumferential edge portion 132 of the metallic cup 131 having a tapered shape for holding the detection element 200 engages the stepped portion 115. A second talc ring 137 is disposed at the base end side of the metallic cup 131 inside the metal shell 110 in a state where the detection element 200 is inserted through the second talc ring 137. A cylindrical sleeve 141 is fitted in the metal shell 110 to press the second talc ring 137 from the base end side. A shoulder portion 142 having a stepped shape is formed at the sleeve 141. An annular crimp packing 143 is disposed at the shoulder portion 142. The crimping portion 118 of the metal shell 110 is crimped to press the shoulder portion 142 of the sleeve 141 toward the leading end side via the crimp packing 143.

The second talc ring 137 pressed against the sleeve 141 is crushed and thoroughly filled in the metal shell 110. The metallic cup 131 and the detection element 200 are positioned and held in the metal shell 110 by means of the second talc ring 137 and the first talc ring 135 that is filled in advance in the metallic cup 131. The airtightness of the metal shell 110 is maintained by the crimp packing 143 sandwiched between the crimping portion 118 and the shoulder portion 142 of the sleeve 141, which crimp packing 143 prevents bleeding of combustion gas.

In the detection element 200, the base end portion 209 of the element protrudes from the crimping portion 118 which serves as a base end portion of the metal shell 110, and a cylindrical separator 145 including insulating ceramic covers the element base end portion 209. The separator 145 internally holds five connection terminals 147 (only one of them is illustrated in FIG. 1), each of which is electrically connected to respective five electrode pads 235 formed on the element base end portion 209 of the detection element 200. Each of the connection terminals 147 is electrically connected to respective five lead wires (only three of them are illustrated in FIG. 1) drawn out to the exterior of the gas sensor 100. The separator 145 accommodates the connection terminals 147 and the lead wires 149 such that the respective connection portions thereof are insulated from one another.

A cylindrical outer sheath 151 is disposed to enclose the separator 145. The outer sheath 151 is generally made of stainless steel (SUS 304 in accordance with Japanese Industrial Standards, in the present embodiment), and a leading end opening portion 152 thereof is disposed radially outside of the base fixing portion 116 of the metal shell 110. The leading end opening portion 152 is attached to the base end fixing portion 116 by crimping the leading end opening portion 152 and laser welding the entire circumference thereof.

In addition, a metal-made cylindrical holding metal fitting 153 is disposed between the outer sheath 151 and the separator 145. The holding metal fitting 153 includes a supporting portion 154 formed by bending the base end of the holding metal fitting 153 inward and then toward the leading end side. The holding metal fitting 153 supports the separator 145 by engaging a collar portion 146 (the collar portion 146 is collar-shaped and provided on the outer circumference at the base end side of the separator 145 inserted into the holding metal fitting), with the supporting portion 154. In this state, the outer sheath 151 at the portion where the holding metal fitting 153 is disposed is crimped from the outside, and the holding metal fitting 153 supporting the separator 145 is fixed to the outer sheath 151.

A grommet 155 made of a fluorine-based rubber is fitted in the base end side opening of the outer sheath 141. The grommet 155 has five insertion holes 156 (only one of them is shown in FIG. 1), and five lead wires 149 extending from the separator 145 are inserted into the respective insertion holes 156 in an airtight state. In this state, the grommet 155 is crimped from outside the outer sheath 151 while pressing the separator 145 to the leading end side, and the grommet is fixed to the outer sheath 151.

The detection element 200 held by the metal shell 110 includes the element protruding portion 202 protruding from the leading end side opening end 110s of the metal shell 110 toward the leading end side. The protector 160 is fitted to the leading end fixing portion 113 and is fixed by laser welding. The protector is configured to protect the element protruding portion 202 of the detection element 200 from staining due to deposits (toxic adhered substances such as fuel ash and oil constituents) in the exhaust gas and breakage due to water. The protector 160 has a double-structure including a cylindrical bottomed inner protector 161 and a cylindrical outer protector 171 configured to enclose the radial periphery of the inner protector 161 via an air gap (clearance).

The inner protector 161 is cylindrical and has a bottom. The inner protector 161 encloses the leading end side (downward in the drawing) and the radial outside (the left and right directions in the drawing) of the element protruding portion 202 of the detection element 200, and is fixed to the metal shell 110 in a state where the element protruding portion 202 is disposed in the interior thereof. A plurality of inner introduction holes 167 are provided on the base end side relative to the leading end 200s (the leading end side end 240s of the porous protection layer 240) of the detection element 200 in the inner protector 161. Each of the inner introduction holes 167 allows introduction of exhaust gas from outside of the inner protector 161 to the inside thereof. In the present embodiment, the diameter of the inner introduction hole 167 is 1.5 mm, for example. The inner introduction hole serves as an introduction hole. The inner protector 161 has a plurality of water drainage holes 166 cut in and opened toward the inside at the leading end side portion of the inner protector 161. The water drainage holes 166 are formed on the leading end side relative to the leading end 200s of the detection element 200. The inner protector 161 has an exhaust hole 164, configured to exhaust gas and water to the outside, that is formed at the center of the bottom wall of the inner protector 161.

The outer protector 171 is fixed to the metal shell 110 in a state where it encloses the radial periphery of the inner protector 161 via an air gap (clearance). The leading end portion 172 of the outer protector 171 is bent inwardly toward the inner protector 161. Therefore, the air gap between the inner protector 161 and the outer protector 171 is closed. A plurality of outer introduction holes 177 is arranged in the circumferential direction at a predetermined position on the leading end side relative to the leading end 200s of the detection element 200 of the outer protector 171. Each of the outer introduction holes 177 allows introduction of exhaust gas from the outside of outer protector 171 to the inside thereof. Plate-shaped guide bodies 178 extending toward the inside are provided in the respective outer introduction holes 177. Therefore, a swirling flow of exhaust gas introduced from the outside into the interior through the outer introduction holes 177 is produced, such that the exhaust gas swirls in the circumferential direction about the axis AX within the air gap defined between the outer protector 171 and the inner protector 161.

Next, the detection element 200 is explained. A porous protection layer 240 comprising porous alumina is coated on outer surfaces of an entire part of the element protruding portion 202 of the detection element 200 and a part of the leading end side of the barrel portion 207.

The porous protection layer 240 includes a diameter-reduced portion 247 such that the thickness of the diameter-reduced portion 247 is gradually reduced toward the base end side (upward in the drawing). As shown in FIG. 4, the diameter-reduced portion 247 is provided in a region of the porous protection layer 240 which is defined in a range equal to or less than the length tk (see FIG. 4) in the axis AX direction from the base end 240k. The length tk is 3 mm or less (e.g., 1 mm in the present embodiment). In the present embodiment, the diameter-reduced portion 247 is tapered such that the thickness thereof is reduced toward the base end side in proportion to the distance in the axis AX direction from the leading end of the diameter-reduced portion 247. The diameter-reduced portion 247 is disposed deeper (toward the base end side) by 3 mm (corresponding to the distance I in FIG. 3) than the leading end side opening portion 110s of the metal shell 110. In other words, although described in greater detail below, the distance I is greater than the minimum clearance H between the metal shell 110 and the coating portion 242 (the base end side coating portion 243).

The coating portion 242 is provided on the leading end side relative to the diameter-reduced portion 247 at the porous protection layer 240 (see FIG. 2 and FIG. 3). The coating portion 242 includes a leading end side coating portion 241 and the base end side coating portion 243. The leading end side coating portion 241 is disposed on the leading end side relative to the leading end side opening end 110s of the metal shell 110 and covers the entirety of the element protruding portion 202. The base end side coating portion covers a part of the leading end side of the barrel portion 207 in the metal shell 110. Therefore, the leading end side coating portion 241 protrudes from the leading end side opening end 110s of the metal shell 110 toward the leading end side. On the other hand, the base end side coating portion 243 is positioned on the base end side relative to the leading end side opening end 110s.

The leading end side coating portion 241 smoothly covers the element protruding portion 202 of the detection element main body 201. That is, the outer surface thereof is free of sharp corners (see FIGS. 2 through 4 and FIG. 6). The corner portions 245 of the leading end side coating portion 241 are rounded.

The thickness dk (see FIG. 4 and FIG. 6) of the coating portion 242 of the porous protection layer 240 is set to be 100 µm or more but 600 µm or less (400 µm in the present embodiment). Also, the minimum clearance G (see FIG. 3) between the porous protection layer 240 and the inner protector 161 is 0.5 mm or more (1 mm in the present embodiment). Further, the minimum clearance H (Refer to FIG. 3) between the porous protection layer 240 (the base end side coating portion 243) and the metal shell 110 is 1.45 mm or less (1.25 mm in the present embodiment). The minimum clearance H is smaller than the diameter of the inner introduction hole 167 of the inner protector 161.

As shown in FIG. 5 and FIG. 6, the detection element main body 201 is formed by simultaneously firing a plurality of layers stacked one upon another. The layers include: a sensor function portion 250 configured to detect a specified gas component; a protection portion 260 stacked on one side of the sensor function portion 250 and configured to protect the sensor function portion 250; and a heater portion 270 stacked on the other side of the sensor function portion 250 and configured to heat the sensor function portion 250 for fast activation.

The sensor function portion 250 includes an oxygen pump cell 251, an oxygen concentration detection cell 253 and an insulating layer 219 stacked therebetween.

The oxygen pump cell 251 includes a first solid electrolyte layer 215, and a first electrode 213 and a second electrode 217, which are respectively formed on both faces of the first solid electrolyte layer 215. The first solid electrolyte layer 215 includes a sintered partially stabilized zirconia body that contains zirconia as a major component with yttria or calcia added as a stabilizing material. A first through hole conductor 215*a* and a second through hole conductor 215*b* are formed at predetermined positions at the base end side of the first solid electrolyte layer 215 and pass through the first solid electrolyte layer 215.

The first electrode 213 contains platinum as a major component and includes: a first electrode portion 213*a* formed at a predetermined position at the leading end side and having a substantially rectangular shape in plan view; and a first lead portion 213*b* extending from the first electrode portion 213*a* toward the base end side. The base end portion of the first lead portion 213*b* is electrically connected to an eighth through hole conductor 211*c* formed at a protection main body layer 211.

The second electrode 217 contains platinum as a major component and includes: a second electrode portion 217*a* formed at a predetermined position at the leading end side and having a substantially rectangular shape in plan view; and a second lead portion 217*b* extending from the first electrode portion 217*a* toward the base end side. The second lead portion 217*b* is electrically connected to a second through hole conductor 215*b* formed at the first solid electrolyte layer 215 and is electrically connected to a fifth through hole conductor 219*b* formed at an insulating layer 219.

The oxygen concentration detection cell 253 includes a second solid electrolyte layer 223, and the third electrode 221 and the fourth electrode 225 respectively formed on opposing faces of the second solid electrolyte layer 223. The second solid electrolyte layer 223 includes a sintered partially stabilized zirconia body that contains zirconia as a major component with yttria or calcia added as a stabilizing material. A third through hole conductor 223*a* is formed at a predetermined position at the base end side of the second solid electrolyte layer 223 and passes through the second solid electrolyte layer.

The third electrode 221 contains platinum as a major component and includes: a third electrode portion 221*a* formed at a predetermined position at the leading end side and having a substantially rectangular shape in plan view; and a third lead portion 221*b* extending from the third electrode portion 221*a* toward the base end side. The base end portion of the third lead portion 221*b* is electrically connected to a fifth through hole conductor 219*b* formed at the insulating layer 219.

The fourth electrode 225 contains platinum as a major component and includes: a fourth electrode portion 225*a* formed at a predetermined position at the leading end side and having a substantially rectangular shape in plan view; and a fourth lead portion 225*b* extending from the fourth electrode portion 225*a* toward the base end side. The base end portion of the fourth lead portion 225*b* is electrically connected to the second through hole conductor 223*a* formed at the second solid electrolyte layer 223.

The insulating layer 219 contains alumina as a major component, and has a gas detection chamber 219*d* formed to penetrate therethrough. The gas detection chamber 219*d* has a substantially rectangular shape in plan view and is provided at a position corresponding to the second electrode portion 217*a* and the third electrode portion 221*a*. The insulating layer 219 also includes diffusion rate controlling portions 220 respectively provided at both sides of the gas detection chamber 219*d* with respect to the width direction thereof. The diffusion rate controlling portions 220 enable gas diffusion between the outside of the element and the gas detection chamber 219*d* under a predetermined rate controlling condition. Each of the diffusion rate controlling portions 220 includes an alumina porous body.

The insulating layer has a fourth through hole conductor 219*a* and a fifth through hole conductor 219*b* penetrating therethrough at predetermined positions at the base end side of the insulating layer 219. The fourth through hole conductor 219*a* is electrically connected to the first through hole conductor 215*a* formed at the first solid electrolyte layer 215, and is also electrically connected to the third through hole conductor 223*a* formed at the second solid electrolyte layer 223. The fifth through hole conductor 219*b* is electrically connected to the second lead portion 217*b* of the second electrode 217 and is also electrically connected to the third lead portion 221*b* of the third electrode 221.

Next, a protection portion 260 is described. The protection portion 260 includes a protection main body layer 211 containing alumina as a major component thereof. The protection main body layer 211 has an opening 211*d* having a substantially rectangular shape in plan view, penetrating therethrough and provided at a position corresponding to the first electrode portion 213*a*. A porous gas introduction portion 212 containing alumina as a major component is provided at the opening 211*d* to close the opening 211*d*.

Three electrode pads 235 are arranged along the width direction at predetermined positions at the base end side on the surface of the protection main body layer 211. A sixth through hole conductor 211*a*, a seventh through hole conductor 211*b* and an eighth through hole conductor 211*c* are respectively formed at predetermined positions at the base end side of the protection main body layer 211 to pass therethrough. The sixth through hole conductor 211*a* is electrically connected to one of the electrode pads 235, and is also electrically connected to the first through hole conductor 215*a* formed at the first solid electrolyte layer 215. The seventh through hole conductor 211*b* is electrically connected to another one of the electrode pads 235, and is also electrically connected to the second through hole conductor 215*b* formed at the first solid electrolyte layer 215. The eighth through hole conductor 211*c* is electrically connected to yet another of the electrode pads 235 and is also electrically connected to the first lead portion 213*b* formed at the first electrode 213.

Next, a heater portion 270 is described. The heater portion 270 includes: a first heater insulating layer 227 having an electrical insulating property; a second heater insulating layer 231 having an electrical insulating property; and an exothermic resistor 229 placed therebetween and configured to generate heat by passing a current therethrough. The first heater insulating layer 227 contains alumina as a major component and is stacked on the sensor function portion 250. The second heater insulating layer 231 contains alumina as a major component.

A ninth through hole conductor 231a and a tenth through hole 231b are respectively formed at predetermined positions at the base end side of the second heater insulating layer 231 to pass therethrough. Two electrode pads 235 are arranged along the width direction at predetermined positions at the base end side on the surface of the second heater insulating layer 231. One electrode pad 235 is electrically connected to the ninth through hole conductor 231a. The other electrode pad 235 is electrically connected to the tenth through hole conductor 231b.

The exothermic resistor 229 includes: a meandering exothermic portion 229a disposed at a predetermined position at the leading end side; a first heater lead portion 229b extending from one end of the exothermic portion 229a toward the base end side; and a second heater lead portion 229c extending from the other end of the exothermic portion 229a to the base end side. The base end portion of the first heater lead portion 229b is electrically connected to the ninth through hole conductor 231a formed at the second heater insulating layer 231. The base end portion of the second heater lead portion 229c is electrically connected to the tenth through hole conductor 231b formed at the second heater insulating layer 231.

Next, a method for manufacturing the gas sensor 100 and the detection element 200 is described. In the following description, post-fired members and pre-fired members corresponding thereto are assigned the same reference numeral for convenience (see FIG. 5 and FIG. 6).

First, a slurry is prepared, which is formed by wet blending to disperse a first raw material powder and a plasticizing agent. The first raw material powder contains alumina powder in an amount of 97 wt % and silica in an amount of 3 wt % as a sintering adjustment agent, and the plasticizing agent contains butyral resin and dibutyl phthalate (DBP). After the slurry is shaped to a sheet by a sheet forming technique using a doctor blade apparatus, the sheet is cut to have a predetermined size to obtain an unfired (green) insulating layer 219 corresponding to the insulating layer 219, an unfired protection main body layer 211 corresponding to the protection main body layer 211, an unfired first heater insulating layer 227 corresponding to the first heater insulating layer 227, and an unfired second heater insulating layer 231 corresponding to the second heater insulating layer 231. Thereafter, a gas detection chamber 219d is formed in the unfired insulating layer 219. In addition, an opening 211d is formed in the unfired protection main body layer 211.

On the other hand, another slurry is prepared, which is formed by wet blending to disperse a second raw material powder and a plasticizing agent. The second raw material powder contains alumina powder in an amount of 63 wt %, silica in an amount of 3 wt % as a sintering adjustment agent and carbon powder in an amount of 34 wt %, and the plasticizing agent contains butyral resin and dibutyl phthalate (DBP). Accordingly, an unfired gas introduction portion 212 corresponding to the gas introduction portion 212 is obtained.

Further, yet another slurry is prepared, which is formed by wet blending to disperse alumina powder (100 wt %) and a plasticizing agent that contains butyral resin and DBP. Accordingly, unfired diffusion rate controlling portions 220 corresponding to the diffusion rate controlling portions 220 are obtained from the slurry.

Yet another slurry is prepared, which is formed by wet blending to disperse a third raw material powder and a plasticizing agent. The third raw material powder contains zirconia powder in an amount of 97 wt % and silica (SiO$_2$ powder and alumina powder, in a total amount of 3 wt %) as a sintering adjustment agent, and the plasticizing agent contains butyral resin and DBP. Accordingly, an unfired first solid electrolyte layer 215 corresponding to the first solid electrolyte layer 215 and the unfired second solid electrolyte layer 223 corresponding to the second electrolyte layer 223 are obtained.

Thereafter, an unfired stacked body is formed by stacking, in the order from below in reference to the elements shown in FIG. 5, the unfired second heater insulating layer 231, an unfired exothermic resistor 229 corresponding to the exothermic resistor 229, the unfired first heater insulating layer 227, an unfired fourth electrode 225 corresponding to the fourth electrode 225, the unfired second solid electrolyte layer 223, an unfired third electrode 221 corresponding to the third electrode 221, the unfired insulating layer 219, the unfired second electrode 217 corresponding to the second electrode 217, the unfired first solid electrolyte layer 215, an unfired first electrode 213 corresponding to the first electrode 213, and the unfired protection main body layer 211.

Specifically, the unfired exothermic resistor 229 is formed on the unfired second heater insulating layer 231 by screen printing using a paste containing platinum as a major component. Then, the unfired first heater insulating layer 227 is stacked on the unfired second heater insulating layer 231 and the unfired exothermic resistor 229.

The unfired fourth electrode 225 is formed on one surface of the unfired second solid electrolyte layer 223 by screen printing using platinum paste containing platinum in an amount of 90 wt % and zirconia powder in an amount of 10 wt %. The unfired second solid electrolyte layer 223 including the unfired fourth electrode 225 is stacked on the unfired first heater insulating layer 227 such that the unfired fourth electrode 225 is sandwiched therebetween. Thereafter, the unfired third electrode 221 is formed on the unfired second solid electrolyte layer 223 by screen printing using platinum paste containing platinum in an amount of 90 wt % and zirconia powder in an amount of 10 wt %.

Next, the unfired insulating layer 219 and the unfired diffusion rate controlling portions 220 are stacked on the unfired second solid electrolyte layer 223 and the unfired third electrode 221. Paste containing carbon as a major component is printed on a portion corresponding to the gas detection chamber 219d after firing.

The unfired second electrode 217 is formed on one surface of the unfired first solid electrolyte layer 215 by screen printing using platinum paste containing platinum in an amount of 90 wt % and zirconia powder in an amount of 10 wt %. The unfired first solid electrolyte layer 215 including the unfired second electrode 217 is stacked on the unfired insulating layer 219 such that the unfired second electrode 217 is sandwiched therebetween. Thereafter, the unfired first electrode 213 is formed on the unfired first solid electrolyte layer 215 by screen printing using platinum paste containing platinum in an amount of 90 wt % and zirconia powder in an amount of 10 wt %.

Next, the unfired protection main body layer 211 is stacked on the unfired first solid electrolyte layer 215 and the unfired first electrode 213. The unfired gas introduction portion 212 corresponding to the gas introduction portion 212 is formed in advance on the unfired protection main body layer 211. Accordingly, the unfired stacked body is thus formed.

Next, after the unfired stacked body is pressed and pressure-fitted at 1 Mpa, it is cut to a predetermined size. Thereafter, resin is removed from the unfired stacked body, and regular firing is carried out in which the unfired stacked body is kept at a firing temperature of 1500° C. for one hour, whereby a detection element main body 201 is obtained.

Figure 7:
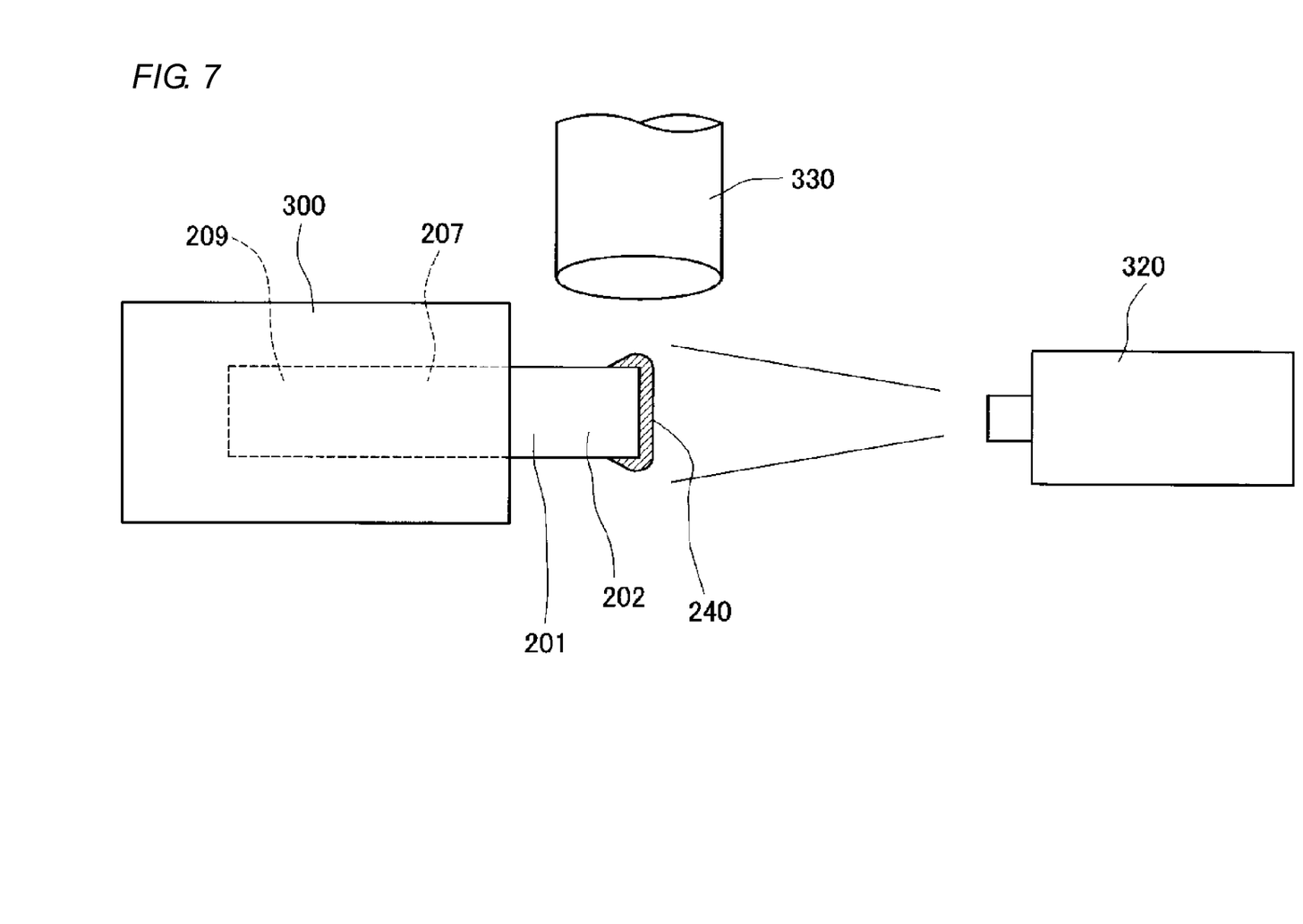
FIG. 7 is a schematic view explaining a method for manufacturing a gas sensor according to the embodiment, and showing a spraying state of a coating solution from the leading end side onto the detection element main body to form an unfired porous protection layer.
Figure 8:
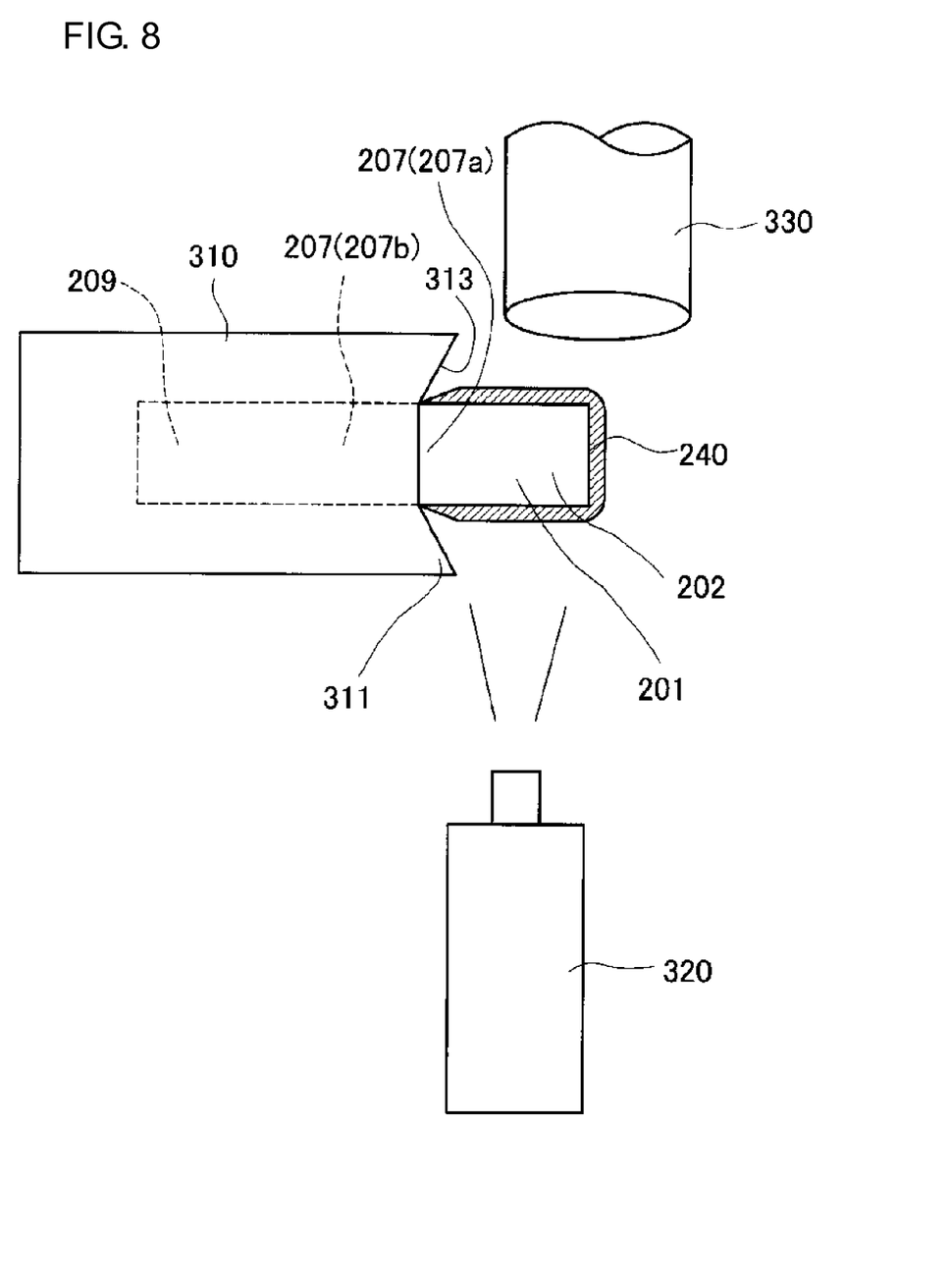
FIG. 8 is a schematic view explaining a method for manufacturing a gas sensor according to the embodiment, and showing a spraying state of a coating solution from the outside in a diametrical direction onto the detection element main body to form an unfired porous protection layer.

Next, spinel powder and titania powder are blended, and are further blended by adding ethanol as a volatile solvent, thereby obtaining a coating solution. As shown in FIG. 7 and FIG. 8, the coating solution is sprayed on the detection element main body 201, and an unfired porous protection layer 240 that becomes a porous protection layer 240 after firing is formed and dried.

Specifically, as shown in FIG. 7, the base end side portion (the barrel portion 207 and the element base end portion 209) of the detection element main body 201 is held by a first holding jig 300 in a state where the element protruding portion 202 of the detection element main body 201 protrudes from the first holding jig 300. Next, a coating solution is coated on the element protruding portion 202 of the detection element main body 201 from the leading end side of the detection element main body 201 by a spraying device 320 using a needle type nozzle. At this time, ceramic powder (i.e., the substance as a residue of the coating solution in which ethanol is evaporated) scattered to the periphery is collected by a suction device 330 disposed radially outside of the detection element main body 201. The ceramic powder collected by the suction device 330 is dispersed in ethanol and reused.

Next, the detection element main body 201 is removed from the first holding jig 300. Next, as shown in FIG. 8, the base end side portion (the barrel portion base end side portion 207b as one part of the barrel portion 207 and the element base end portion 209) of the detection element main body 201 is held by a second holding jig 310 in a state where the element protruding portion 202 of the detection element main body 201 and the barrel leading end side portion 207a as the other part of the leading end side of the barrel portion 207 protrude from the second supporting jig 310. The second holding jig 310 includes a protruding portion 311 that defines a cone-shaped recess portion 313 at the leading end thereof. By spinning the second holding jig 310 around the axis thereof, the coating solution is coated on the detection element main body 201 by a spraying device 320 disposed radially outside of the detection element main body 201 while spinning the detection element main body 201 around the axis thereof. Since a volatile solvent is evaporated at the time when the coating solution is adhered to the surface of the detection element main body 201, a layer made of dried ceramic raw material powder is formed on the surface of the detection element main body 201 (the element protruding portion 202 and the barrel portion leading end side portion 207a).

The second holding jig 310 includes the protruding portion 311 that serves as a barrier configured to gradually reduce the amount of the coating solution toward the base end side which is coated on the base end side portion (in the vicinity of the second holding jig 310) of the barrel portion leading end side portion 207a of the detection element main body 201. This portion becomes a diameter-reduced portion after firing.

Next, the temperature of the detection element main body 201 in this state is raised under atmospheric conditions and is subjected to thermal processing with a maximum temperature maintained at 1000° C. for one hour. Thereafter, the detection element main body 201 is air cooled, whereby the detection element 200 including the porous protection layer 240 is obtained.

The detection element 200 produced by the above-described method is inserted into a metallic cup 131 and is then fixed with a ceramic ring 133 and the first talc ring 135, thereby forming an assembly. Next, the assembly is inserted into the metal shell 110 to which the protector 160 is attached, and then the second talc ring 137, the sleeve 141 and the crimping packing 143 are inserted. The assembly is crimped at the crimping portion 118 of the metal shell 110, thereby forming a lower assembly. On the other hand, the outer sheath 151, separator 141, grommet 155, etc., are assembled thereto, thereby forming an upper assembly. Thereafter, the lower assembly and the upper assembly are attached to complete the gas sensor 100.

As described above, in the present embodiment, since the diameter-reduced portion 247 of the porous protection layer 240 is tapered such that the thickness thereof is gradually reduced toward the base end side, the diameter-reduced portion 247 is free of sharp corners. Therefore, it is possible to prevent chipping of the diameter-reducing portion 247 when the gas sensor is subjected to vibration and shock in use which would otherwise thin the porous protection layer 240 at the chipped portion or expose the detection element main body 201 at the chipped portion. Accordingly, the detection element main body 201 is hardly subjected to cracking even though water drops in the exhaust gas adhere to the diameter-reduced portion 247. In addition, the diameter-reduced portion 247 is disposed on the base end side relative to the inner introduction hole 167 of the inner protector 161 that surrounds the porous protection layer 240. Consequently, water drops that pass through the inner introduction hole 167 hardly adhere to the diameter-reduced portion 247. Therefore, the detection element main body 201 of the gas sensor 100 is effectively protected from cracking.

The length tk along the axis AX direction of the diameter-reduced portion 247 of the porous protection layer 240 is the thickness dk of the coating portion 242 or more but 3 mm or less. Therefore, it is possible to reliably prevent chipping of the diameter-reduced portion 247 due to vibration and shock of the gas sensor in use.

The thickness dk of the coating portion 242 of the porous protection layer 240 is 100 μm or more. Therefore, an effect of the porous protection layer 240, such as an effect of preventing cracks caused by adhesion of water drops, can be sufficiently obtained. On the other hand, when the thickness dk of the coating portion 242 of the porous protection layer 240 is 600 μm or less, the activation time required for the detection element 200 to reach an activation temperature upon heating by the exothermic resistor 229 can be sufficiently shortened, and consumption power of the exothermic resistor 229 can be reduced. Also, the detection sensitivity of the detection element 200 is enhanced.

The coating portion 242 of the porous protection layer 240 smoothly covers the element protruding portion 202 of the detection element main body 201. Therefore, chipping of the coating portion 242, due to vibration and shock of the gas sensor in use, can be prevented.

In the present embodiment, the minimum clearance G between the coating portion 242 and the inner protector 161 is 0.5 mm or more. Therefore, water drops hardly adhere to the coating portion 242 even if the water drops enter the inner protector 161 along with gas to be detected. Also, water drops adhering to the inner circumferential surface of the inner protector 161 can be prevented from contacting the coating portion 242. Therefore, it is possible to reliably prevent cracking of the detection element 200 due to thermal shock when water drops adhere.

The diameter-reduced portion 247 is disposed within the metal shell 110. Therefore, the metal shell 110 functions as a barrier, and water drops hardly adhere to the diameter-reduced portion 247. Accordingly, the gas sensor 100 can effectively prevent cracking of the detection element main body 201.

The minimum clearance H between the metal shell 110 and the coating portion 242 is 1.45 mm or less. Therefore, water drops hardly adhere to the diameter-reduced portion 247 even if the water drops enter the inside of the inner protector 161 along with gas to be detected. Accordingly, it is possible to reliably prevent cracking of the detection element main body 201 due to thermal shock when water drops adhere.

The distance I between the leading end side opening end 110s of the metal shell 110 and the diameter-reduced portion 247 is greater than the minimum clearance H between the metal shell 110 and the coating portion 242. Therefore, water drops hardly adhere to the diameter-reduced portion 247 even if the water drops enter the interior of the inner protector 161 along with gas to be detected. Accordingly, it is possible to reliably prevent cracking of the detection element main body 201 due to thermal shocks when water drops adhere. Further, even when the minimum clearance H between the metal shell 110 and the coating portion 247 is smaller than the diameter of the inner introduction hole 167, water drops hardly adhere to the diameter-reduced portion 247, which can prevent cracking of the detection element main body 201.

Although the above description was given according to an embodiment of the present invention, the present invention is not limited thereto. It is a matter of course that various modes of carrying out the principles disclosed herein may be adopted without departing from the spirit and scope of the claims appended hereto.

For example, the above-described embodiment exemplified a full-range air-fuel ratio sensor as the gas sensor 100. However, the present invention may also be applied to other gas sensors such as an oxygen sensor, an NOx sensor, a HC sensor, etc.

Although the exemplified protector 160 of the embodiment has a double wall structure including an inner protector 161 and an outer protector 171, the protector 160 may have a single wall structure.

In the above embodiment, the coating portion 242 is exemplified as a structure including a leading end side coating portion 241 that covers the entirety of the element protruding portion 202 and a base end side coating portion 243 that covers a part of the leading end side of the barrel portion 207 within the metal shell 110. However, the structure may be such that the diameter-reduced portion 247 is exposed toward the leading end side from the leading end side opening end 110s of the metal shell 110, and the coating portion 242 includes only a leading end side coating portion 241 to cover a part of the element protruding portion 202. In this case, the diameter-reduced portion 247 is disposed on the base end side relative to the inner introduction hole 167 of the inner protector 161.

This application is based on Japanese Patent Application No. 2007-270607 filed Oct. 17, 2007 and Japanese Patent Application No. 2008-210347 filed Aug. 19, 2008, the above applications incorporated herein by reference in their entirety.

What is claimed is:

1. A gas sensor comprising:
a cylindrical metal shell extending along an axial direction from a leading end thereof to a base end thereof;
a plate-shaped detection element main body extending along the axial direction from a leading end thereof to a base end thereof and held radially inside the metal shell, the detection element main body comprising an element protruding portion protruding from the leading end of the metal shell in the axial direction;
a porous protection layer coated on a leading end portion of the detection element main body; and
a protector attached to the metal shell and comprising a side wall surrounding the element protruding portion in a radial direction perpendicular to the axial direction without intervention of other member, the side wall having introduction holes formed therein which allow gas to be introduced into an inner space which includes the element protruding portion defined by the sidewall,
wherein the porous protection layer comprises: a first portion; and a second portion provided on a base end side with respect to the first portion, the second portion having a progressively reduced thickness in a direction toward the base end of the detection element main body,
wherein the second portion of the porous protection layer is disposed closer to the base end of the detection element than the introduction holes in the axial direction;
wherein the introduction holes are disposed at a same position as the element protruding portion in the axial direction;
wherein the introduction holes are disposed at a same position as the first portion of the protection layer in the axial direction so as to quicken response time of the gas sensor;
wherein the entire part of the second portion of the protection layer is disposed closer to the base end of the detection element than all of the introduction holes in the axial direction so as to suppress cracking of the protection layer due to water droplets passing through the introduction holes of the sidewall; and
wherein the second portion is disposed within the metal shell.

2. The gas sensor according to claim 1, wherein a length of the second portion of the porous protection layer of progressively reduced thickness in the axial direction is not less than a thickness of the first portion of the porous protection layer but not more than 3 mm.

3. The gas sensor according to claim 1, wherein the thickness of the first portion is not less than 100 μm but not more than 600 μm.

4. The gas sensor according to claim 1, wherein the first portion has a smoothly curved outer shape in cross section.

5. The gas sensor according to claim 1, wherein a minimum clearance between the first portion and the protector is 0.5 mm or more.

6. The gas sensor according to claim 1, wherein a minimum clearance between the metal shell and the first portion is 1.45 mm or less.

7. The gas sensor according to claim 1, wherein a distance between the second portion and the leading end of the metal shell is greater than the minimum clearance between the metal shell and the first portion.

8. The gas sensor according to claim 1, wherein a minimum clearance between the metal shell and the first portion is smaller than a diameter of the introduction holes.

9. The gas sensor according to claim 1, wherein the second portion of the porous protection layer has a taper shape.

10. A gas sensor comprising:
a cylindrical metal shell extending along an axial direction from a leading end thereof to a base end thereof;
a plate-shaped detection element main body extending along the axial direction from a leading end thereof to a base end thereof and held radially inside the metal shell, the detection element main body comprising an element protruding portion protruding from the leading end of the metal shell in the axial direction;
a porous protection layer coated on a leading end portion of the detection element main body; and a protector attached to the metal shell and comprising a side wall surrounding the element protruding portion in a radial direction perpendicular to the axial direction without intervention of other member, the side wall having introduction holes formed therein which allow gas to be introduced into an inner space which includes the element protruding portion defined by the sidewall, wherein the porous protection layer comprises: a first portion; and a second portion provided on a base end side with respect to the first portion, the second portion having a progressively reduced thickness in a direction toward the base end of the detection element main body, wherein the second portion of the porous protection layer is disposed closer to the base end of the detection element than the introduction holes in the axial direction;

wherein the introduction holes are disposed at a same position as the element protruding portion in the axial direction;

wherein the introduction holes are disposed in line of sight at a same position as the first portion of the protection layer in the axial direction so as to quicken response time of the gas sensor;

wherein the entire part of the second portion of the protection layer is disposed closer to the base end of the detection element than all of the introduction holes in the axial direction so as to suppress cracking of the protection layer due to water droplets passing through the introduction holes of the sidewall; and wherein the second portion is disposed within the metal shell.

* * * * *